United States Patent [19]
Sen et al.

[11] Patent Number: 6,114,574
[45] Date of Patent: Sep. 5, 2000

[54] PREPARATION OF AROMATIC ACIDS

[75] Inventors: Ayusman Sen; Anne Pifer, both of State College, Pa.

[73] Assignee: The Penn State Research Foundation, University Park, Pa.

[21] Appl. No.: 09/313,833

[22] Filed: May 18, 1999

Related U.S. Application Data

[60] Provisional application No. 60/085,993, May 19, 1998.

[51] Int. Cl.[7] .................................................. C07C 51/16
[52] U.S. Cl. .............................................. 562/410
[58] Field of Search ................................ 502/410

[56] References Cited

U.S. PATENT DOCUMENTS

| | | | |
|---|---|---|---|
| 2,766,281 | 10/1956 | Zienty et al. | 260/524 |
| 3,219,691 | 11/1965 | McNelis . | |
| 3,235,587 | 2/1966 | Boffa et al. . | |
| 3,532,746 | 10/1970 | Ember . | |
| 3,626,001 | 12/1971 | Keith . | |
| 3,686,293 | 8/1972 | Gualdi et al. . | |
| 4,145,560 | 3/1979 | Alagy et al. . | |
| 4,605,763 | 8/1986 | Kiefer et al. . | |
| 5,557,009 | 9/1996 | Izumisawa et al. . | |

OTHER PUBLICATIONS

Panov, et al, *Applied Catalysis A: General*, vol. 82, pp. 31–36 (1992).

*Primary Examiner*—Paul J. Killos
*Attorney, Agent, or Firm*—Thomas J. Monahan

[57] ABSTRACT

A process for converting alkyl-substituted aromatic hydrocarbons, such as p-xylene or 2,6-dimethyl naphthalene to their corresponding dicarboxylic acids is disclosed, said process comprising contacting the alkyl-substituted aromatic hydrocarbon with a gaseous mixture containing oxygen, NOx, where x is 1 or 2, and an inert gas, and heating the resulting mixture at a temperature from 90 ° C. to 250 ° C. and at a pressure of from 300 psi to 2500 psi for a period of time sufficient to convert the alkyl substitutents on the aromatic hydrocarbons to carboxyl groups.

20 Claims, No Drawings

PREPARATION OF AROMATIC ACIDS

This application claims benefit of provisional application Ser. No. 60/085,993 filed May 19, 1998. Research performed in connection with the subject matter of this application has been funded, at least in part, by the Department of Energy (DOE) under contract DE-FG07-96ER14694.

BACKGROUND OF THE INVENTION

This invention relates to an improved process for the preparation of aromatic acids from alkyl-substituted aromatic hydrocarbons. More particularly, the invention relates to an improved process for preparing aromatic acids, such as naphthalene-2,6-dicarboxylic acid or terephthalic acid, by means of a $NO_x$-mediated oxidation of alkyl side chains on an aromatic nucleus. In the case of terephthalic acid, for example, the invention relates to the $NO_x$-mediated oxidation of the methyl groups of p-xylene to carboxyl groups.

Organic acids, such as naphthalene-2,6-dicarboxylic acid or terephthalic acid, are highly useful in the manufacture of polyester-type and polyamide-type resins, including polyethyleneterephthalate. Such organic acids customarily have been prepared by a liquid phase oxidation of an alkyl-substituted aromatic precursor in the presence of an aqueous acidic reaction medium, and usually in the presence of a metal catalyst. For example, U.S. Pat. No. 2,766,281 discloses the preparation of phthalic acids, including terephthalic acid, by a step-wise oxidation of a corresponding xylene with concentrated nitric acid at atmospheric pressure and in the presence of an inert organic reaction medium that is liquid at the reaction temperatures. In the first step, the xylene starting material is reacted with the nitric acid at a temperature of from about 120 ° C. up to the boiling point of the xylene starting material, while removing water by distillation, to form a toluic acid. In the second step, nitric acid is slowly added to the toluic acid at a temperature in excess of about 140 ° C., while removing water by distillation, to form the product phthalic acid.

Another patent that discloses the use of nitric acid as the oxidizing agent for converting p-xylene to terephthalic acid is U.S. Pat. No. 3,235,587. In that patent, it is disclosed to add excess nitric acid having a concentration of between 5% and 15% into a reactor, under superatmospheric pressure and at temperatures between 1500 ° C. and 200 ° C., and then to add the p-xylene into the reactor. The use of catalytic amounts of copper powder and ammonium metavanadate is said to facilitate the oxidation process.

Using oxygen or an oxygen-containing gas as the oxidizing agent in place of nitric acid has been disclosed. For example, U.S. Pat. No. 3,626,001 discloses a two-stage process for preparing terephthalic acid or isophthalic acid from the corresponding xylene. In the first stage, a feed comprising the xylene, an alkanoic acid solvent, a molecular oxygen-containing gas and a cobalt catalyst are heated to form a first stage product comprising substantial amounts of toluic acid. In the second stage, the first stage product is heated in a mixture with a alkanal corresponding to the alkanoic acid of the first-stage feed, a molecular oxygen-containing gas and a cobalt catalyst. Preferably, the alkanoic acid used in the first stage of the process is acetic acid, and the alkanal used in the second stage is acetaldehyde.

Numerous others patents discloses metal catalyzed processes which use acetic acid as the reaction medium during the oxidation of alkyl-substituted aromatic compounds to their corresponding acids. See, for example, U.S. Pat. Nos. 3,686,293; 4,145,560; 4,605,763; and 5,557,009, the disclosures of which are incorporated herein by reference.

U.S. Pat. No. 3,532,746 relates to a multi-stage process for preparing aromatic polycarboxylic acids having at least four carboxylic acid groups as nuclear substituents in at least two vicinal pairs. The process involves oxidizing an acid-precursor with molecular oxygen in the presence of an organic solvent, preferably acetic acid, bromine and a heavy metal oxidation catalyst, and in the further presence of an oxidation catalyst providing NO having an oxidation potential of −1.0 to −0.5 selected from nitric acid and inorganic nitrates and nitrites, such as calcium nitrate, sodium nitrite, barium nitrite and ammonium nitrate.

U.S. Pat. No. 3,219,691 relates to the preparation of pure naphthalene-2,6-dicarboxylic acid from an impure mixture of naphthalene dicarboxylic acids prepared by the liquid phase partial oxidation of mixed naphthalenes at a temperature above 140 ° C. by means of $NO_2$ in the presence of a selenium catalyst. The process of preparing the impure acid mixture involves adding selenium to an alkyl naphthalene starting material in a trichlorobenzene solvent and then bubbling $NO_2$ into reaction mixture at a temperature of 225 ° C. until a 50% excess of $NO_2$ has been added. The reaction mixture is then washed successively with trichlorobenzene, pentane and water at room temperature to form an impure acid mixture containing on the order of 85% diacids by weight.

The use of $N_2O$ as the stoichiometric oxidant at high concentrations (up to 20% of the gas mixture) for the conversion of benzene to phenol is known. See, for example, Appl. Catal. A 1992, 82,31.

While prior art processes have been successful in preparing aromatic polycarboxylic acids, in general, and phthalic acids, e.g., terephthalic acid, in particular, they generally have required the use of expensive catalysts and/or the use of significant quantities of acetic acid or other solvent, some of which is consumed and needs to be replaced.

SUMMARY OF THE INVENTION

The present invention provides an improved process for the preparation of aromatic polycarboxylic acids, in general, and of phthalic acids, e.g., terephthalic acid, in particular, by an $NO_x$-mediated oxidation of alkyl side chains on an alkyl-substituted aromatic starting material. The improved process comprises contacting the alkyl-substituted aromatic starting material at an elevated temperature and pressure with a gas mixture containing oxygen, $NO_x$ and nitrogen. The process may be performed in more than one stage at varying temperatures, and may be performed in the presence or absence of a solvent. In one preferred embodiment, the process comprises a solvent-less, two stage process for converting p-xylene to terephthalic acid. In the first stage, p-xylene is converted primarily to p-toluic acid; and in the second stage, p-toluic acid is converted to terephthalic acid. In another embodiment, 2,6-dimethyl naphthalene is converted in a similar manner to naphthalene-2,6-dicarboxylic acid. The process of the invention may be performed successfully without the need for any heavy metal oxidation catalyst.

DETAILED DESCRIPTION

The present invention provides an improved process for the preparation of aromatic polycarboxylic acids from alkyl-substituted aromatic hydrocarbons having up to 14 nuclear carbon atoms. In one aspect of the invention, the alkyl-substituted aromatic hydrocarbon is a xylene, e.g., p-xylene, and the polycarboxylic acid product comprises a phthalic acid, e.g., terephthalic acid. With respect to the preparation of terephthalic acid in accordance with the present invention, p-xylene (i.e., 1,4-dimethylbenzene) is oxidized by contacting p-xylene with a gas mixture comprising oxygen, $NO_x$, and an inert gas, preferably nitrogen, at a temperature of from about 90 ° C. to 250 ° C. and a pressure of from about 300 to about 2500 psi.

The oxygen-containing gas, for example molecular oxygen or air, may be added to the reaction zone either at room temperature, or at a temperature close to that prevailing in the reaction zone. Similarly, the $NO_x$, and inert gas may be added to the reaction zone either at room temperature, or at a temperature close to that prevailing in the reaction zone. The $NO_x$, as used in this specification and claims, is meant to describe a gas containing NO and/or $NO_2$ as an essential component. The ratio of the partial pressure of $O_2$ to $NO_x$ in the reaction zone typically would range from about 1:10 to about 10:1. However, the ratio preferably would be from about 1:2 to 7:1, e.g., from 1:1 to 5:1. The ratio of the partial pressure of the inert gas, e.g., $N_2$, to $O_2$ typically would range from about 15:1 to 1:1, and preferably from about 10:1 to 2:1, e.g., from 8:1 to 4:1.

The process may be performed in a single stage or, if desired, in two stages. Similarly, the process may take place either in the presence or absence of a solvent. In one preferred embodiment, p-xylene, in the absence of a solvent, is oxidized in a single stage by heating the p-xylene, while in contact with an oxygen-containing gas, $NO_x$ and nitrogen in a suitable pressure vessel, at a temperature of about 90 ° C. to about 250° C. and a pressure of about 300 to about 2500 psi, until both of the methyl groups on the p-xylene molecule are oxidized to carboxyl groups. Typically this would take from about 1 hour to about 50 hours, or more; and more typically from about 10 to about 40 hours.

In another preferred embodiment, the process would be performed in two stages, wherein a first of the methyl groups on the p-xylene molecule would be converted to a carboxyl group in the first stage, and the second methyl group would be convert in the second stage. In the latter embodiment, the p-xylene would be converted to p-toluic acid in the first stage reaction zone at a temperature of from about 90° C. to about 160 ° C., typically about 120° C.; and the p-toluic acid would be converted to terephthalic acid in the second stage reaction zone at a temperature of from about 160 ° C. to 250 ° C., typically about 180° C.

In another preferred embodiment, 2,6-dimethyl naphthalene is converted to naphthalene-2,6-dicarboxylic acid in accordance with the procedures described above in connection with the conversion of p-xylene to terephthalic acid.

The process of the invention may be performed in the presence of an inert solvent, such as hexane or the like. However, the use of a solvent has been found to be unnecessary, and it is often preferred to perform the process in the absence of a solvent. This greatly simplifies the subsequent isolation of the acid products and, of course, saves on the cost of solvent.

The process of the invention is illustrated by a series of runs in which p-xylene was oxidized to terephthalic acid. The oxidation reaction was carried out in two stages in a 300 ml high-pressure reactor equipped with a glass liner. As indicated in Table 1, the first stage oxidation reaction took place at 120 ° C., and the second stage oxidation reaction took place at 180 ° C. The reaction time for each stage and for each run is shown in Table 1. Table 1 also shows the amount of p-xylene (in ml) and the partial pressure of $O_2$, NO and $N_2$ (in psi) charged to the reactor, the time of the reaction (in hours), the temperature of the reaction (in ° C.), the % conversion of the p-xylene to toluic acid and terephthalic acid, and the ratio of terephthalic acid to p-toluic acid in the product mixture.

TABLE 1

Oxidation of P-Xylene by $NO_x/O_2$

| p-Xylene (ml) | NO | $O_2$ | $N_2$ | Time (Hr)/Temp. (°C.) | % Conversion | Ratio* |
|---|---|---|---|---|---|---|
| 1 | 20 | 100 | 800 | 1st stage: 16/120<br>2nd stage: 24/180 | 76 | 2 |
| 1 | 100 | 100 | 800 | 1st stage: 4/120<br>2nd stage: 17/180 | 87 | 5 |
| 1 | 100 | 200 | 800 | 1st stage: 15/120<br>2nd stage: 7/180 | 92 | 4 |

* = ratio of terephthalic acid/p-toluic acid

What is claimed is:

1. A process for the oxidation of an alkyl-substituted aromatic hydrocarbon having up to 14 nuclear carbon atoms, comprising contacting the alkyl-substituted aromatic hydrocarbon with a gas mixture comprising oxygen, $NO_x$, where x is 1 or 2, and an inert gas at a temperature of from 90 ° C. to 250 ° C. and at a pressure of from 300 psi to 2500 psi for a period of time sufficient to convert alkyl substituents on said aromatic hydrocarbon to carboxyl groups.

2. The process according to claim 1, wherein said alkyl substituents comprise methyl groups and wherein the oxidation is performed in a single stage.

3. The process according to claim 1, wherein said alkyl substituents comprise methyl groups and wherein the oxidation is performed in a two stages at two different temperatures.

4. The process according to claim 3, wherein said alkyl-substituted aromatic hydrocarbon comprises a xylene or an alkyl-substituted naphthalene, wherein the first stage oxidation is performed at a temperature of from 90 ° C. to 160° C., and wherein the second stage oxidation is performed at a temperature of from 160 ° C. to 250 ° C.

5. The process according to claim 3, wherein said alkyl-substituted aromatic hydrocarbon is p-xylene; and wherein at least a portion of the p-xylene is oxidized in said first stage to p-toluic acid, and wherein said p-toluic acid is oxidized in said second stage to terephthalic acid.

6. The process of according to claim 1, wherein said alkyl-substituted aromatic hydrocarbon is 2,6-dimethyl naphthalene, and wherein said oxidation is performed in a single stage to convert said 2,6-dimethyl naphthalene to naphthalene-2,6-dicarboxylic acid.

7. The process of according to claim 1, wherein said alkyl-substituted aromatic hydrocarbon is 2,6-dimethyl naphthalene, and wherein said oxidation is performed in two stages to convert said 2,6-dimethyl naphthalene to naphthalene-2,6-dicarboxylic acid, wherein the first stage oxidation is performed at a temperature of from 90 ° C. to 160 ° C., and wherein the second stage oxidation is performed at a temperature of from 160° C. to 250° C.

8. The process according to claim 5, wherein the first and second stage oxidation reactions are performed in the presence of an inert solvent.

9. The process according to claim 5, wherein the first and second stage oxidation reactions are performed in the absence of a solvent.

10. The process according to claim 7, wherein the first and second stage oxidation reactions are performed in the presence of an inert solvent.

11. The process according to claim 7, wherein the first and second stage oxidation reactions are performed in the absence of a solvent.

12. A process for conversion of p-xylene to terephthalic acid, which comprises the steps of:

(a) providing liquid p-xylene in a reaction zone;

(b) adding a gas mixture comprising oxygen, NOx, where x is 1 or 2, and an inert gas to the reaction zone, such that the pressure in the reaction zone is from 300 psi to 2500 psi; and (c) heating the contents of the reaction zone to a temperature of from 90° C. to 250° C. for a period sufficient to convert at least a portion of the p-xylene to terephthalic acid.

13. The process according to claim 12, wherein the heating step (c) is performed in two stages (c1) and (c2), wherein the first stage (c1) comprises heating the contents of the reaction zone to a temperature of from 90° C. to 160° C. for a period sufficient to convert at least a portion of the p-xylene to p-toluic acid, and wherein the second stage (c2) comprises heating the contents of the reaction zone to a temperature of from 160° C. to 250° C. for a period sufficient to convert at least a portion of the p-toluic acid to terephthalic acid.

14. The process according to claim 12, wherein said inert gas is nitrogen.

15. The process according to claim 13, wherein said inert gas is nitrogen.

16. The process according to claim 12, performed in the absence of a solvent.

17. The process according to claim 13, performed in the absence of a solvent.

18. The process according to claim 12, performed in the presence of a solvent.

19. The process according to claim 13, performed in the presence of a solvent.

20. A process for conversion of 2,6-dimethyl naphthalene to naphthalene-2,6-dicarboxylic acid, which comprises the steps of:

(a) introducing 2,6-dimethyl naphthalene to a reaction zone;

(b) adding a gas mixture comprising oxygen, NOx, where x is 1 or 2, and an inert gas to the reaction zone, such that the pressure in the reaction zone is from 300 psi to 2500 psi; and (c) heating the contents of the reaction zone to a temperature of from 90° C. to 250° C. for a period sufficient to convert at least a portion of the 2,6-dimethyl naphthalene to naphthalene-2,6-dicarboxylic acid.

* * * * *